United States Patent [19]

Wade et al.

[11] 4,127,587
[45] Nov. 28, 1978

[54] TRIAZOLYLBENZOPHENONES

[75] Inventors: Peter C. Wade, Pennington; Thomas P. Kissick, Princeton, both of N.J.

[73] Assignee: E. R. Squibb & Sons, Inc., Princeton, N.J.

[21] Appl. No.: 868,765

[22] Filed: Jan. 12, 1978

Related U.S. Application Data

[62] Division of Ser. No. 825,640, Aug. 18, 1977, Pat. No. 4,093,728.

[51] Int. Cl.² ............................................. C07D 249/08
[52] U.S. Cl. ................................................. 260/308 R
[58] Field of Search ..................................... 260/308 R

[56] References Cited

U.S. PATENT DOCUMENTS 4,000,151  12/1976  Hester ............................ 260/308 R
4,007,219  2/1977   Hassall et al. .................. 260/308 R Primary Examiner—Alton D. Rollins Attorney, Agent, or Firm—Lawrence S. Levinson; Merle J. Smith; Burton Rodney

[57] ABSTRACT

Triazoloisoindoles are provided having the structure

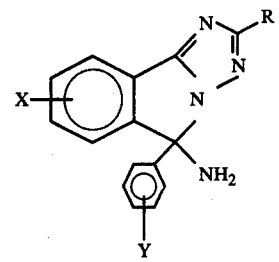

wherein X, Y and R are as defined hereinafter. These compounds have antiinflammatory activity and anthelmintic activity. Pharmaceutical compositions containing such compounds and methods for using such compounds are also provided.

5 Claims, No Drawings

TRIAZOLYLBENZOPHENONES

This is a division, of application Ser. No. 825,640, filed Aug. 18, 1977 now U.S. Pat. No. 4,093,728 issued June 6, 1978.

The present invention relates to triazoloisoindoles which are useful as antiinflammatory agents and anthelmintic agents and to pharmaceutical compositions containing the same, and to methods for using the same.

The triazoloisoindoles of the invention have the following structure:

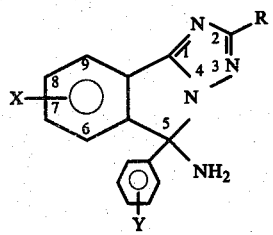

wherein X is hydrogen, halogen, lower alkyl, lower alkoxy, trifluoromethyl or nitro; Y is hydrogen, halogen, lower alkyl, lower alkoxy, nitro, or trifluoromethyl; R is hydrogen, lower alkyl, trifluoromethyl or phenyl.

The preferred compounds of the invention are those of formula I wherein X is halogen and is in the 7-position, Y is hydrogen and R is lower alkyl.

The term "lower alkyl" as used herein refers to alkyl groups having 1 to 4 carbons, with methyl and ethyl being preferred.

The term "lower alkoxy" as used herein refers to lower alkyl groups as defined above attached to an oxygen atom, with methoxy being preferred.

The term "halogen" as employed herein refers to chlorine, bromine, iodine or fluorine with chlorine and bromine being preferred.

The triazoloisoindoles of the invention of formula I are prepared by reacting a 3-phenyl-1,2,4-triazole of the structure

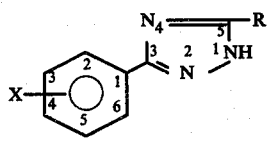

with a strong base, such as an organometallic base like an alkyllithium or aryllithium in the presence of a non-reacting solvent, such as tetrahydrofuran, preferably at temperatures ranging from −100° to 30° C. A benzonitrile of the structure

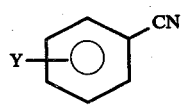

is added with stirring and a proton source, such as ammonium chloride, ammonium sulfate, ammonium bromide, dimethylamine hydrochloride or trimethylamine hydrochloride is added to produce the compound of formula I.

The compounds of formula I are easily hydrolyzed to the corresponding benzophenone (formula Ia) by warming with aqueous acid, aqueous base or on standing in the presence of aqueous acid or base for several hours at room temperature.

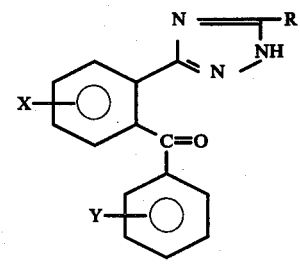

The formula Ia compounds are novel and have the same utility as the formula I compounds as described above.

The product of the reaction using the formula II compounds wherein X is in the 3-position will yield a mixture of compounds of formula I wherein X is in the 6- or 8-position (or formula I); these compounds may be separated chromatographically or by crystallization.

The starting materials of structure II are known in the art or easily prepared by conventional procedures. For example, they may be prepared according to the procedure outlined in German (East) Patent No. 67,130 (1969), Chem. Abstr. 71, 12441 e. Thus, a benzonitrile of the structure

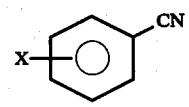

is condensed with an amino-1,2,4-triazole of the structure

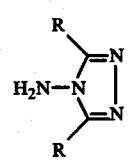

in the presence of an alkali metal hydride, such as sodium hydride or lithium hydride, and a non-reacting solvent, such as dimethylsulfoxide (DMSO), dimethylformamide, or tetrahydrofuran, to form a compound of the structure

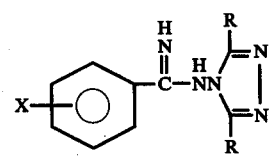

which is then reacted with acetic anhydride to form

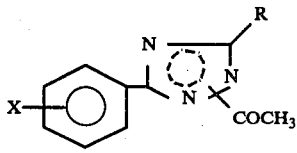

The acetyltriazole of structure VII is refluxed in water to form the structure II material.

The starting triazole of structure V is prepared by techniques well known in the art (e.g., see Th. Curtius and G. M. Dedichen, *J. Prakt. Chem.*, 50, 241 (1894), Beil. 26, 29). Thus, the formula V compound may be prepared by reaction of hydrazine and an alkylcyanide

R'CN     (VIII)

wherein $R^1$ is lower alkyl at temperatures ranging from 100° to 250° C. for periods of 0.5 to 48 hours in a sealed vessel, if necessary.

The compounds of formula I have antiinflammatory activity as measured by the reverse passive arthus (RPA) or other related tests (M. B. Goldlust and W. F. Schreiber, Agents and Actions, 5, 39 (1975)) and are useful as antiinflammatory agents and may be used, for example, in a manner similar to phenylbutazone or indomethacin. They may be used to decrease joint swelling, tenderness, pain and stiffness in mammalian species, e.g., in conditions such as rheumatoid arthritis. The quantity administered ranges from about 1 mg to about 150 mg per kg of body weight per day.

The compound or mixture of compounds of formula I of their pharmaceutically acceptable acid-addition salts may be administered orally or parenterally in a conventional dosage form, such as tablet, capsule, injectable or the like. These may be conventionally formulated in an oral or parenteral dosage form by compounding with a conventional vehicle, excipient, binder, preservative, stabilizer, flavor or the like as called for by accepted pharmaceutical practice.

The compounds of formula I also have anthelmintic activity and are useful in the treatment and/or prevention of helminthiasis, a parasitic disease which causes widespread and often serious infection in domesticated animals such as swine, horses, cattle, dogs, cats and sheep. The compounds are useful in treating infections caused by Haemonchus, Ostertagia, Trichostrongylus, Cooperia, Dictyocaulus, Nematodirus, Bunostomum, Strongyloides, Oesophagostomum, Trichuris, Moniezia, and liver flukes (for example in sheep). In treating domesticated animals, the compounds are given orally; however, other routes such as parenterally, for example, subcutaneously, intravenously, interperitoneally and intramuscularly may be employed.

Where the compounds are administered orally, they may be mixed with a nontoxic, edible carrier to form a feed supplement, or be administered in unit dosage forms such as powders, capsule, tablet, boluses, drenches, etc.

In general, the compounds of formula I exhibit anthelmintic activity when administered to animals (parenterally or orally) in a single dose of about 1 to about 100 mg per kilogram of animal body weight. It is preferred to employ in the range of 2.5-25 mg per kilogram of body weight. The compounds may be divided into a plurality of smaller doses given parenterally or orally over one or more days.

When the compounds of formula I are to be administered in unit dosage form, capsules, boluses or drenches containing the desired amount of anthelmintic distributed in a pharmaceutically acceptable vehicle are usually employed. These are prepared by intimately and uniformly mixing the active ingredient with suitable finely divided diluents, suspending agents, fillers, disintegrating agents and/or binders such as starch, lactose, talc, magnesium stearate, vegetable gums and the like and are compounded by techniques generally known in the art.

The compounds of formula I may also be administered as a component of the feed of the animals. Thus, novel feed and feed supplement compositions may be prepared in which the compounds of this invention are present as an active anthelmintic ingredient. A typical feed supplement comprises the anthelmintic agent intimately dispersed in or admixed with an inert carrier or diluent, i.e., one that is nonreactive with respect to the anthelmintic agent and that may be administered with safety to the animals. The carrier or diluent is preferably one that is or may be an ingredient of an animal ration. This composition may be mixed with the feed to give any useful desired concentration, preferably about 0.1-2%. Lastly, feeds containing the active ingredient may be made directly by mixing said active ingredient in a feed which is inert to said anthelmintic compounds so as to give feeds having concentrations of anthelmintic agent of from 0.1-2%.

The following examples are provided for illustrative purposes and may include particular features of the invention, however the examples should not be construed as limiting the invention, many variations of which are possible without departing from the spirit or scope thereof. All temperatures are in degrees centigrade.

EXAMPLE 1

7-Chloro-2-methyl-5-phenyl-5H-[1,2,4]triazolo-[5,1-a]-isoindol-5-amine

A. 4-Amino-3,5-4H,1,2,4-dimethyltriazole (Th. Curtius and G. M. Dedichen, *J. Prakt. Chem.*, 50, 241 (1894))

Hydrazine hydrate (100 g, 2.0 mol) and acetonitrile (75 g, 1.8 mol) are placed in a 1 l. bomb which is sealed and heated at 150° for 8 hours. The reaction mixture is heated at 180° (pressure rises to 420 psi) overnight. The bomb is cooled, vented and opened to yield a white solid plus some liquid. The solid is collected on a filter, washed with a small amount of cold water, toluene, and recrystallized from 600 ml of ethyl acetate to give 51 g of the title A compound, m.p. 195°-197°.

B. 4-Chloro-N-(3,5-dimethyl-4H-1,2,4-triazol-4-yl)-benzenecarboximidamide

Sodium hydride [15.32 g (0.364 mol) of a 57% oil dispersion] is washed with ether (X 5) in a sintered glass funnel to remove the oil. The free sodium hydride is washed with a little DMSO into a stirred suspension of 50.0 g (0.363 mol) 4-chlorobenzonitrile and 40.7 g (0.363 mol) 4-amino-3,5-4H,1,2,4-dimethyltriazole (prepared in Part A) in 200 ml of DMSO (distilled from $CaH_2$ under vacuum). After the addition the mixture is stirred in an ice bath for 1 hour and for 3 hours at room temperature. The reaction mixture is poured into 2 liters of ice water and stirred for 15 minutes until the flocculant precipitate coagulates into a filterable state. The product is then filtered out, washed with water, and dried at 50° under vacuum overnight to yield 94.2 g of the title compound, m.p. 303°–306°.

The crude compound (6.0 g) is digested with isopropanol; filtered off and dried to yield 4.1 g of pure title B compound, m.p. 310°–312°.

C. 3-(4-Chlorophenyl)-5-methyl-1,2,4-triazole (H. Becker et al. East German Pat. No. 67,130 (1969), Chem. Abst.71, 124441e)

63.6 g (0.254 mol) of 4-Chloro-N-(3,5-dimethyl-4H-1,2,4-triazol-4-yl)benzenecarboximidamide and 67 ml of acetic anhydride in a 300 ml round bottom flask equipped with a distillation head are heated to 170° in an oil bath. A melt forms from which acetic acid is distilled off. The mixture is refluxed for 2.5 hours and the excess acetic anhydride is removed under vacuum. The residue is triturated with 120 ml of water, and filtered. The filter cake is dissolved in 1 liter of hot absolute ethanol, filtered hot, and the product precipitated from the hot alcohol by adding 3 liters of cold water. The product is filtered off, washed with water, and dried at 80° under vacuum to yield 37.6 g of an N-acetyl triazole, m.p. 132°–133°.

27.0 g (0.114 mol) Of the above N-acetyl triazole is refluxed in 800 ml of water for 9 hours (reaction followed by TLC) and stirred overnight at room temperature. The product is filtered out, washed with water, and dried at 90° under vacuum overnight to yield 23.4 g of the title C compound, m.p. 173°–175°.

D. 7-Chloro-2-methyl-5-phenyl-5H-[1,2,4]-triazolo[5,1-a]isoindol-5-amine 2.0 g (10.3 mmol) of 3-(4-Chlorophenyl)-5-methyl-1,2,4-triazole is dissolved in 50 ml of tetrahydrofuran (THF) (freshly distilled from lithium aluminum hydride) mechanically stirred in a 250 ml round-bottom 3-necked flask equipped with a septum and nitrogen inlet and cooled in an ice bath. 13.6 ml (22.7 mmol) of n-butyllithium (1.67 mol/liter in hexane) is injected with a syringe and the mixture is stirred in the ice bath for 30 minutes. 2.12 g (20.6 mmol) of benzonitrile is added in a little THF. After stirring for 30 minutes in the ice bath and for 30 minutes at room temperature, the mixture is poured into a chilled stirred mixture of 100 ml of 2.5 M ammonium chloride and 200 ml of chloroform. The layers are separated and the aqueous layer washed with chloroform. The combined chloroform layers are washed with water and dried ($Na_2SO_4$). The chloroform is removed under vacuum and the residue is recrystallized from toluene to yield 1.5 g of the title compound, m.p. 173°–175°.

EXAMPLES 2 to 15

Following the procedure of Example 1 but substituting for the first benzonitrile, the compound shown in Column I of Table A below, substituting for the aminotriazole, the compound shown in Column II, and substituting for the second benzonitrile, the compound shown in Column III, the compound of the invention shown in Column IV is obtained.

TABLE A

| | column I | column II | column III | column IV | | |
|---|---|---|---|---|---|---|
| | 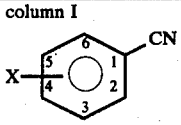 | 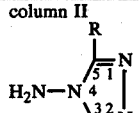 | 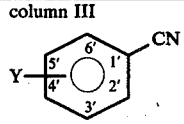 | 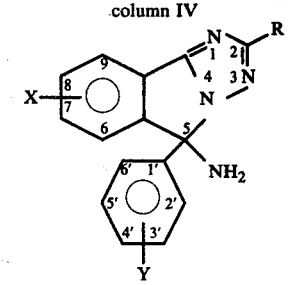 | | |
| Ex. No. | X (position) | R | Y (position) | X (position) | R | Y (position) |
| 2. | H | $CH_3$ | $CH_3$(2) | H | As in Column II | As in Column III |
| 3. | Br(3) | $C_2H_5$ | H | mixture of Br(6) and (8) | | |
| 4. | $CH_3$(3) | $CF_3$ | $C_2H_5$(3) | mixture of $CH_3$ (6) and (8) | | |
| 5. | $CH_3O$(4) | $C_2H_5$ | Cl(4) | $CH_3O$(7) | | |
| 6. | $CF_3$(3) | $CF_3$ | $CF_3$(3) | mixture of $CF_3$ (6) and (8) | | |
| 7. | $NO_2$(4) | n-$C_3H_7$ | $CH_3O$(2) | $NO_2$(7) | | |
| 8. | H | $C_2H_5$ | $NO_2$(3) | H | | |
| 9. | Cl(2) | n-$C_4H_9$ | $C_2H_5$(2) | Cl(9) | | |
| 10. | $C_2H_5$(2) | $(CH_3)_2CHCH_2$ | t-$C_4H_9$(4) | $C_2H_5$(9) | | |
| 11. | $C_2H_5O$(4) | n-$C_4H_9$ | Br(2) | $C_2H_5O$(7) | | |
| 12. | $NO_2$(4) | $CH_3$ | Cl(2) | $NO_2$(7) | | |
| 13. | $CF_3$(4) | $C_2H_5$ | H | $CF_3$(7) | | |
| 14. | H | $CH_3$ | H | H | | |
| 15. | H | H | H | H | | |

EXAMPLE 16

5-Chloro-2-(5-methyl-1H-1,2,4-triazol-3-yl)-benzophenone

Ten milligrams of 7-chloro-2-methyl-5-phenyl-5H-[1,2,4]triazolo-[5,1-a]-isoindol-5-amine (as prepared in Example 1) are refluxed for 10 minutes in 2 ml of 50% aqueous methanol containing a drop of acetic acid. The methanol is removed under vacuum and the aqueous residue made basic with 10% NaOH. The aqueous solution is washed with chloroform, neutralized with 10% HCl and extracted with chloroform. The chloroform solution is evaporated to dryness and the residue is recrystallized from a water-ethanol mixture, m.p. 149° to 150°.

EXAMPLES 17 to 30

Following the procedure of Example 16, but substituting the product of Examples 2 to 15 as set out in Column I of Table B shown below, the benzophenone shown in Column II is obtained. In the case of Examples 18, 19 and 21, the starting materials comprised of mixtures of compounds wherein X is at the (6) and (8) positions (Examples 3, 4 and 6) are separated by chromatographic procedures and the (8) isomers are employed herein.

TABLE B

| | Column I | | | Column II | | |
|---|---|---|---|---|---|---|
| Ex. No. | X (position) | R | Y (position) | X (position) | R | Y (position) |
| 17. | H | CH$_3$ | CH$_3$(2) | H | As in Column I | |
| 18. | Br(8) | C$_2$H$_5$ | H | Br(4) | | |
| 19. | CH$_3$(8) | CF$_3$ | C$_2$H$_5$(3) | CH$_3$(4) | | |
| 20. | CH$_3$O(6) | C$_2$H$_5$ | Cl(4) | CH$_3$O(6) | | |
| 21. | CF$_3$(8) | CF$_3$ | CF$_3$(3) | CF$_3$(4) | | |
| 22. | NO$_2$(7) | n-C$_3$H$_7$ | CH$_3$O(2) | NO$_2$(5) | | |
| 23. | H | C$_2$H$_5$ | NO$_2$(3) | H | | |
| 24. | Cl(9) | n-C$_4$H$_9$ | C$_2$H$_5$(2) | Cl(3) | | |
| 25. | C$_2$H$_5$(9) | (CH$_3$)$_2$CHCH$_2$ | t-C$_4$H$_9$(4) | C$_2$H$_5$(3) | | |
| 26. | C$_2$H$_5$O(7) | n-C$_4$H$_9$ | Br(2) | C$_2$H$_5$O(5) | | |
| 27. | NO$_2$(7) | CH$_3$ | Cl(2) | NO$_2$(5) | | |
| 28. | CF$_3$(7) | C$_2$H$_5$ | H | CF$_3$(5) | | |
| 29. | H | CH$_3$ | H | H | | |
| 30. | H | H | H | H | | |

What is claimed is:

1. A compound of the structure

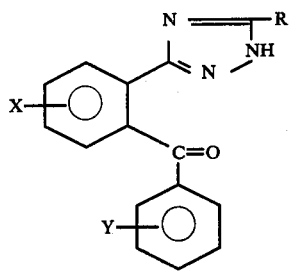

wherein X is hydrogen, halogen, lower alkyl, lower alkoxy, trifluoromethyl or nitro; Y is hydrogen, halogen, lower alkyl, lower alkoxy, trifluoromethyl or nitro; and R is hydrogen, lower alkyl or trifluoromethyl.

2. The compound of claim 1 wherein X is hydrogen, halogen or lower alkyl.

3. The compound of claim 1 wherein Y is hydrogen, halogen, or trifluoromethyl.

4. The compound of claim 1 wherein R is lower alkyl or trifluoromethyl.

5. The compound of claim 1 having the name 5-chloro-2-(5-methyl-1H-1,2,4-triazol-3-yl)benzophenone.

* * * * *